United States Patent [19]

Slaugh

[11] Patent Number: 5,043,516

[45] Date of Patent: Aug. 27, 1991

[54] OLEFIN ETHYLATION PROCESS

[75] Inventor: Lynn H. Slaugh, Houston, Tex.

[73] Assignee: Shell Oil Company, Houston, Tex.

[21] Appl. No.: 617,738

[22] Filed: Nov. 26, 1990

[51] Int. Cl.$^5$ .............................................. C07C 2/02
[52] U.S. Cl. ...................... 585/533; 585/510; 585/643; 585/645
[58] Field of Search ................ 585/510, 533, 643, 645

[56] References Cited

U.S. PATENT DOCUMENTS

| | | | |
|---|---|---|---|
| 2,492,693 | 12/1949 | Freed | 260/683.15 |
| 3,175,020 | 3/1965 | Wilkes | 260/683.15 |
| 3,651,161 | 9/1969 | Waragai et al. | 260/671 C |
| 3,676,523 | 7/1972 | Mason | 260/683.15 D |
| 3,686,351 | 8/1972 | Mason | 260/683.15 D |
| 3,737,475 | 6/1973 | Mason | 260/683.15 D |
| 3,825,615 | 7/1973 | Lutz | 260/683.15 |
| 4,020,121 | 4/1977 | Kister et al. | 260/683.15 D |
| 4,288,649 | 9/1981 | McCaulay | 585/533 |
| 4,505,787 | 3/1985 | Fuller et al. | 204/67 |
| 4,511,748 | 4/1985 | Kudoh et al. | 585/467 |
| 4,544,790 | 10/1985 | Drake | 585/516 |
| 4,609,637 | 9/1986 | Drake | 502/174 |
| 4,661,466 | 4/1987 | Drake et al. | 502/184 |

FOREIGN PATENT DOCUMENTS 1269280  8/1969  United Kingdom .

OTHER PUBLICATIONS

Pines, et al., "Sodium Catalyzed Reactions, II., Side--Chain Ethylation of Alkyl Aromatic Hydrocarbons Catalyzed by Sodium," J. of the American Chemical Society, vol. 77, 1955, pp. 554-559.

*Primary Examiner*—Curtis R. Davis
*Attorney, Agent, or Firm*—Pamela J. McCollough

[57] ABSTRACT

The present invention provides a process for the ethylation of detergent-range olefins to produce higher molecular weight olefins which comprises reacting ethylene with a detergent-range olefin in the presence of a catalyst comprising an alumina having a sodium content per unit surface area of less than about $3 \times 10^{-5}$ g/m$^2$.

18 Claims, No Drawings

OLEFIN ETHYLATION PROCESS

FIELD OF THE INVENTION

This invention relates to a process for the ethylation of detergent-range olefins with a catalyst comprising an alumina having a sodium content per unit surface area of less than about $3 \times 10^{-5}$ g/m$^2$.

BACKGROUND OF THE INVENTION

Various processes for the alkylation of olefins employing alkali metal catalysts alone or supported on suitable carriers, together with certain promoters have previously been reported. U.S. Pat. No. 2,492,693 discloses the use of an alkali metal (sodium) catalyst and a polynuclear aromatic hydrocarbon promoter for the intermolecular condensation of different monoolefins. In the *Journal of American Society*, vol. 77, pp. 554–559 (1955), the reaction of alkyl aromatic compounds with ethylene takes place in the presence of a sodium catalyst and an organic compound promoter. British Patent No. 2,269,280 discloses alkylating an aromatic hydrocarbon with a monoolefin in the presence of a catalyst prepared by dispersing an alkali metal on a potassium compound. U.S. Pat. No. 4,511,748 discloses a process for alkylating aromatic hydrocarbons with olefins using a catalyst comprising sodium and/or sodium amide on a potassium carbonate carrier.

Other known process for the dimerization of olefins employing potassium as catalyst component are found in U.S. Pat. No. 3,175,020, which discloses catalysts having potassium metal on a alumina carrier; and U.S. Pat. Nos. 4,609,637, 4,661,466, 4,544,790 and 4,505,787 which teach the use of elemental alkali metals deposited on potassium carbonate catalyst supports.

U.S. Pat. No. 3,651,161 discloses a process for the alkylation of compounds with an active hydrogen, allylic or benzylic, and the use of sodium/pyrene charge transfer complex or a potassium/biphenyl charge transfer complex.

It has now been found that a catalyst comprising an alumina having a sodium content per unit surface area of less than about $3 \times 10^{-5}$ g/m$^2$, when properly activated, promotes an ethylation reaction in which ethylene is added to detergent-range olefins to produce more-branched olefins of higher molecular weight.

SUMMARY OF THE INVENTION

The present invention provides a process for the ethylation of detergent-range olefins to produce higher molecular weight olefins which comprises reacting ethylene with a detergent-range olefin in the presence of a catalyst comprising an alumina having a sodium content per unit surface area of less than about $3 \times 10^{-5}$ g/m$^2$.

DESCRIPTION OF THE PREFERRED EMBODIMENTS

The present invention relates to a process for ethylating detergent range olefins by contacting a detergent-range olefin with ethylene in the presence of a catalyst comprising an alumina having a sodium content per unit surface area of less then about $3 \times 10^{-5}$ g/m$^2$. The detergent range olefins are ethylated in the instant invention to prepare more-branched olefins having higher molecular weights. As used herein, "ethylation" and "ethylating" refer to the addition of one or more ethyl moieties (CH$_3$CH$_2$—) to an organic substrate which in the instant specification is an olefin. In a preferred embodiment, straight-chain olefins can be converted to mono-branched olefins having an ethyl group pendant to the main chain, or if desired, multi-branched products can be obtained.

The detergent range olefins suitable for use in the present invention are olefins having from about 8 to about 22 carbon atoms, preferably from about 8 carbon atoms to about 18 carbon atoms. These olefins can be alpha olefins or internal olefins and they may be linear or branched. Single cut olefins or mixtures of olefins may also be used. In a particularly preferred embodiment, the olefin contains from about 12 to about 18 carbon atoms.

Preferred for use as olefin reactant for the practical reason of availability are the commercial olefin products in the C$_8$ to C$_{22}$ range. One such example of such olefins is the Chevron Alpha Olefin product series (trademark of and sold by Chevron Chemical Co.), manufactured by the cracking of paraffin wax. Commercial production is more commonly accomplished by the oligomerization of ethylene using procedures well known in the art. The resulting oligomerization products are substantially of linear structure and thus products are substantially of linear structure. Commercial olefin products manufacture by ethylene oligomerization are marketed in the United States by Shell Chemical Company under the trademark Neodene and by Ethyl Corporation as Ethyl Alpha-olefins. Specific procedures for preparing suitable linear olefins from ethylene are described in U.S. Pat. Nos. 3,676,523, 3,686,351, 3,737,475, 3,825,615 and 4,020,121. While most of such olefin products are comprised largely of alpha-olefins, higher linear internal olefins are also commercially produced, for example, by the chlorination-dehydrochlorination of paraffins, by paraffin dehydrogenation, and by isomerization of alpha-olefins. Linear internal olefin products in the C$_8$ to C$_{22}$ range are marketed by Shell Chemical Company and by Liquichemica Company. These commercial products, whether predominantly internal or alpha-olefins typically contain about 70 percent by weight or more, most often about 80 percent by weight or more, linear monoolefins in a specified carbon number range (e.g., C$_{10}$ to C$_{12}$, C$_{11}$ to C$_{15}$, C$_{12}$ to C$_{13}$, C$_{15}$ to C$_{18}$, etc.), the remainder of the product being olefin of other carbon number or carbon structure, diolefins, paraffins, aromatics, and other impurities resulting from the synthesis process. C$_8$ to C$_{14}$ olefins are considered the most preferred olefins for use in the instant invention.

The catalysts utilized for the reaction of ethylene with a detergent-range olefin in the instant invention are aluminas. The alumina employed can be any of the variety of available aluminas or alumina hydrates, such as alumina gel, activated alumina, gamma alumina and the like. The most suitable aluminas for use in the present invention are found to be those having a sodium content per unit surface area of less than about $3 \times 10^{-5}$ g/m$^2$, preferably less than about $2.5 \times 10^{-5}$ g/m$^2$ area and more preferably, less than about $2 \times 10^{-5}$ g/m$^2$, and having surface areas ranging from about 10 m$^2$/g to about 500 m$^2$/g, preferably from about 50 m$^2$/g to about 400 m$^2$/g. In a preferred embodiment, the alumina is a gamma alumina. Aluminas are readily available commercially which are suitable for use in the instant invention. The following table lists several commercial gamma aluminas and their properties which are suitable.

| Alumina | Surface Area, m²/g | Pore Vol. cc/gm | Na % wt. | Na content per unit surface area, g/m² | SO₄ % wt. | Fe₂O₃ % wt. | Cl⁻ % wt. |
| --- | --- | --- | --- | --- | --- | --- | --- |
| CCI (a) | 252 | 0.8 | 0.016 | $0.06 \times 10^{-5}$ | 0.06 | — | 0.02 |
| KA-201 (b) | 325 | 0.42 | 0.33 | $1.0 \times 10^{-5}$ | 0.03 | — | 0.01 |
| RA-201 (c) | 263 | 0.26 | 0.47 | $1.8 \times 10^{-5}$ | 0.02 | 0.18 | — |
| ACCP (d) | 225 | 0.68 | 0.058 | $0.26 \times 10^{-5}$ | 0.6 | — | 0.6 |
| Norton | 218 | 0.62 | 0.0051 | $0.02 \times 10^{-5}$ | 0.03 | — | 0.03 |
| SCS 250 (e) | 250 | 0.57 | 0.046 | $0.2 \times 10^{-5}$ | — | 0.025 | — |
| SCS 59 (e) | 59 | 0.60 | 0.054 | $0.92 \times 10^{-5}$ | — | 0.025 | — |

(a) Catalysts & Chemicals, Inc., now United Catalysts
(b) Kaiser
(c) Reynolds Corporation
(d) American Cyanamid Corporation
(e) Pechney-Saint-Gobain The process of the instant invention can be carried out using either batch or continuous types of operation, although the catalysts of the instant invention are particularly well suited for continuous or fixed bed operation. Suitable equipment such as, for example, autoclaves, tubular reactors and the like can be employed. Materials such as steel, stainless steel, glass-lined reactors and the like can be employed.

The reaction temperatures and pressures can vary depending on the olefin feed employed and the products desired. Typically, a temperature in the range of from about 150° C. to about 400° C. and a pressure in the range of from about 200 psig to about 3000 psig is suitable. The temperature is preferably in the range of from about 150° C. to about 300° C., and more preferably in the range of from about 200° C. to about 250° C. The pressure is preferably in the range of from about 500 psig to about 2000 psig, and more preferably in the range of from about 800 psig to about 1200 psig. As the reaction temperatures and pressures are lowered, the conversion is lowered. If, for example, a monoethylated olefin is desired, it will be necessary to limit the feed conversion by lowering the temperature and pressure as the initial monoethylated olefin can undergo further ethylation. Temperatures in the range of from about 150° C. to about 250° C. and pressures in the range of from about 800 psig to about 1200 psig are most preferred as they result in a minimal amount of by-products from side reactions such as dimerization and polymerization.

The ethylation reaction is usually carried out in a liquid phase and if desired, solvents or diluents for the reactants can be used. Suitable diluents include saturated aliphatic hydrocarbons, e.g., pentane, hexane, cyclohexane; and aromatic compounds such as benzene and toluene.

The contact time required for the ethylation reaction depends upon several factors such as temperature, pressure, the level of conversion desired and the like. The length of time during which the ethylene and the detergent-range olefin are contacted with the catalyst are usually between about one hour and about twenty hours, although shorter and longer contact times can be utilized. Preferably, the contact times are in the range of from about two hours to about ten hours. When the reaction is carried out in continuous fashion, the reactant/catalyst contact time may be expressed in terms of the liquid hourly space velocity (volume of reactants per volume of catalyst per hours, LHSV). The LHSV is suitably in the range of from about 0.1 to 5.0, preferably from about 0.5 to about 1.0 LHSV.

The relative amounts of olefin reactant and ethylene are such that an ethylation product is produced which has the desired degree of branching in the carbon chain. In general, the olefin is contacted with sufficient ethylene for a sufficient time to yield a mixture of ethylated olefins characterized as the addition product of an average of between about 1.0 and 1.3 mols of ethylene per mole of olefin. Addition of greater amounts of olefin results in a larger portion of more-branched products. An excess of olefin reactant results in the production of ethylated olefins having primarily one added ethyl branch in the molecule. Preferably, the olefin reactant is used in such an excess that of the olefin reactant molecules, no more than about 50%, preferably no more than about 20%, and more preferably, no more than about 15% react with two or more ethylene molecules to yield ethylated olefins having more than one added ethyl branch and/or an added branch of more than 2 carbon atoms. Maintaining a relatively low conversion, e.g., 10-20%, of olefin reactant during ethylation also aids in preventing the formation of polyethylated products.

The more-branched, higher molecular weight olefin products prepared according to the present process are useful in a wide variety of applications such as, for example, making a broad range of surfactants, including nonionic, anionic, cationic and amphoteric surfactants. The olefin products prepared according to the instant invention are particularly useful for making surfactant materials which have superior cold water detergency and better handling characteristics than their linear counterparts.

The ranges and limitations provided in the instant specification and claims are those which are believed to particularly point out and distinctly claim the present invention. It is, however, understood that other ranges and limitations which perform substantially the same function in substantially the same way to obtain the same or substantially the same result are intended to be within the scope of the instant invention as defined by the instant specification and claims.

The instant invention is illustrated by the following examples which are provided as illustration and are not to be construed as limiting the invention.

ILLUSTRATIVE EMBODIMENTS

Ethylation Process

These examples illustrate the use of alumina catalysts in a series of ethylation reactions in which a detergent-range olefin, 1-dodecene was contacted and reacted with ethylene to produce more-branched higher molecular weight olefins.

In Example 1, 30 milliliters of 1-dodecene was charged to a one-liter autoclave, under nitrogen blanket, together with 6 grams of the Kaiser grade A-201 alumina (14-30 mesh) catalyst. After thoroughly flushing with nitrogen and evacuating, the autoclave was charged with 800 psig ethylene. The autoclave contents were then heated under stirring to about 250° C. As the ethylation reaction commenced, ethylene was added to maintain a total pressure in the range of from about 500-800 psig. After about 5 hours, the reaction was terminated and the autoclave contents were allowed to cool to room temperature. A total of 31 grams of reactants and catalyst were removed and then filtered to separate catalyst. The properties of the catalyst and the results are presented in Table I.

59 was used as the alumina catalyst. The properties of the catalysts and the results are presented in Table I.

For Comparative Example A, the ethylation of 1-dodecene was carried out according to the same procedures, and using the same quantities of catalyst and olefin reactant, as described for Example 1, with the exception that a Kaiser grade A-201 alumina having a sodium content per unit surface area greater than about $3 \times 10^{-5}$ g/m$^2$ was used as catalyst. The properties of the catalyst and the results are presented in Table I.

For Comparative Example B, the ethylation of 1-dodecene was carried out according to the same procedures, and using the same quantities of catalyst and olefin reactant, as described for Example 1, with the exception that an SCS 59 alumina having a sodium content per unit surface area greater than about $3 \times 10^{-5}$ g/m$^2$ was used as catalyst. The properties of the catalyst and the results are presented in Table I.

TABLE I

ETHYLATION OF 1-DODECENE

| | % wt. Na | Surface Area (m$^2$/g) | Na Content Per Unit Surface Area (g/m$^2$) | Temp. (°C.) | Press. (psig) | 1-Dodecene Conv., % | Selectivity, Mole % | | | |
|---|---|---|---|---|---|---|---|---|---|---|
| | | | | | | | $C_{14}H_{28}$ | $C_{16}H_{32}$ | $C_{18}H_{36}$ | $C_{20}H_{40}$ |
| Example 1 | 0.33 | 325 | $1 \times 10^{-5}$ | 250 | 800 | 32.6 | 55.3 | 43.6 | 1.1 | — |
| Example 2 | 0.33 | 325 | $1 \times 10^{-5}$ | 200 | 800 | 10 | 86 | 14 | — | — |
| Example 3 | 0.33 | 325 | $1 \times 10^{-5}$ | 151 | 800 | 3 | 100 | — | — | — |
| Example 4 | 0.39 | 325 | $1.2 \times 10^{-5}$ | 250 | 800 | 27.8 | 58 | 42 | — | — |
| Example 5 | 0.62 | 325 | $1.9 \times 10^{-5}$ | 250 | 800 | 11.8 | 89.1 | 11.9 | — | — |
| Example 6 | 0.94 | 325 | $2.9 \times 10^{-5}$ | 250 | 800 | 6.5 | 98.3 | 1.7 | — | — |
| Example 7 | 0.046 | 250 | $0.2 \times 10^{-5}$ | 250 | 800 | 72 | 3.9 | 45.2 | 42.2 | 8.7 |
| Example 8 | 0.054 | 59 | $0.9 \times 10^{-5}$ | 250 | 800 | 22.2 | 66.9 | 33.1 | — | — |
| Example 9 | 0.11 | 59 | $1.9 \times 10^{-5}$ | 250 | 800 | 8.9 | 88.2 | 11.8 | — | — |
| Comparative Example A | 1.5 | 325 | $4.6 \times 10^{-5}$ | 250 | 800 | 0.6 | 100 | — | — | — |
| Comparative Example B | 0.32 | 59 | $5.4 \times 10^{-5}$ | 250 | 800 | 0.93 | 100 | — | — | — |

For Example 2, the ethylation of 1-dodecene was carried out according to the same procedures, and using the same quantities of catalyst and olefin reactant, as described for Example 1, with the exception that the temperature was 200° C. The properties of the catalyst and the results are presented in Table I.

For Example 3, the ethylation of 1-dodecene was carried out according to the same procedures, and using the same quantities of catalyst and olefin reactant, as described for Example 1, with the exception that the temperature was 151° C. The properties of the catalyst and the results are presented in Table I.

For Examples 4-6, the ethylation of 1-dodecene was carried out according to the same procedures, and using the same quantities of catalyst and olefin reactant, as described for Example 1, with the exception that Kaiser grade A-201 aluminas having different sodium contents were utilized as catalysts. The properties of the catalysts and the results are presented in Table I.

For Example 7, the ethylation of 1-dodecene was carried out according to the same procedures, and using the same quantities of catalyst and olefin reactant, as described for Example 1, with the exception that SCS 250 was used as the alumina catalyst. The properties and results are presented in Table I.

For Examples 8-9, the ethylation of 1-dodecene was carried out according to the same procedures, and using the same quantities of catalyst and olefin reactant, as described for Example 1, with the exception that SCS As can be seen in Table I, relatively low conversions result in primarily mono-ethylated product. It can also be seen that deeper conversions result in an increase in branching. In addition, the results in Table I show that the 1-dodecene conversions obtained in Examples 1-9 are much better than those obtained in Comparative Examples A and B where aluminas having sodium contents per unit surface area greater than about $3 \times 10^{-5}$ g/m$^2$ were used.

What is claimed is:

1. A process for ethylating detergent range olefins which comprises contacting a detergent-range olefin with ethylene in the presence of a catalyst comprising an alumina having a sodium content per unit surface area of less than about $3 \times 10^{-5}$ g/m$^2$.

2. The process of claim 1 wherein said alumina is a gamma alumina.

3. The process of claim 1 wherein said alumina catalyst has a sodium content per unit surface area of less than about $2.5 \times 10^{-5}$ g/m$^2$.

4. The process of claim 3 wherein said alumina catalyst has a sodium content per unit surface area of less than about $2 \times 10^{-5}$ g/m$^2$.

5. The process of claim 1 wherein said alumina catalyst has a surface area in the range of from about 10 m$^2$/g to about 500 m$^2$/g.

6. The process of claim 5 wherein said alumina catalyst has a surface area in the range of from about 50 m$^2$/g to about 400 m$^2$/g.

7. The process of claim 1 wherein said detergent-range olefin is an olefin having from about 8 to about 22 carbon atoms.

8. The process of claim 7 wherein said detergent-range olefin is an olefin having from about 8 to about 18 carbon atoms.

9. The process of claim 1 wherein said ethylation is carried out at a temperature in the range of from about 150° C. to about 400° C. and a pressure in the range of from about 200 psig to about 3000 psig.

10. The process of claim 9 wherein said ethylation is carried out at a temperature in the range of from about 150° C. to about 300° C. and a pressure in the range of from about 500 psig to about 2000 psig.

11. A process for ethylating detergent range olefins which comprises contacting a detergent-range olefin with ethylene in the presence of a catalyst comprising a gamma alumina having a sodium content per unit surface area of less than about $3 \times 10^{-5}$ g/m$^2$ at a temperature in the range of from about 150° C. to about 400° C. and a pressure in the range of from about 200 psig to about 3000 psig.

12. The process of claim 11 wherein said alumina catalyst has a sodium content per unit surface area of less than about $2.5 \times 10^{-5}$ g/m$^2$.

13. The process of claim 12 wherein said alumina catalyst has a sodium content per unit surface area of less than about $2 \times 10^{-5}$ g/m$^2$.

14. The process of claim 11 wherein said alumina catalyst has a surface area in the range of from about 10 m$^2$/g to about 500 m$^2$/g.

15. The process of claim 14 wherein said alumina catalyst has a surface area in the range of from about 50 m$^2$/g to about 400 m$^2$/g.

16. The process of claim 11 wherein said detergent-range olefin is an olefin having from about 8 to about 22 carbon atoms.

17. The process of claim 16 wherein said detergent-range olefin is an olefin having from about 8 to about 18 carbon atoms.

18. The process of claim 11 wherein said ethylation is carried out at a temperature in the range of from about 150° C. to about 300° C. and a pressure in the range of from about 500 psig to about 2000 psig.

* * * * *